US011527312B2

(12) United States Patent
Ghosh et al.

(10) Patent No.: US 11,527,312 B2
(45) Date of Patent: Dec. 13, 2022

(54) CLINICAL REPORT RETRIEVAL AND/OR COMPARISON

(71) Applicant: KONINKLIJKE PHILIPS N.V., Eindhoven (NL)

(72) Inventors: Erina Ghosh, Boston, MA (US); Oladimeji Feyisetan Farri, Yorktown Heights, NY (US)

(73) Assignee: Koninklijke Philips N.V., Eindhoven (NL)

( * ) Notice: Subject to any disclaimer, the term of this patent is extended or adjusted under 35 U.S.C. 154(b) by 179 days.

(21) Appl. No.: 16/300,271

(22) PCT Filed: May 3, 2017

(86) PCT No.: PCT/EP2017/060478

§ 371 (c)(1),
(2) Date: Nov. 9, 2018

(87) PCT Pub. No.: WO2017/198461

PCT Pub. Date: Nov. 23, 2017

(65) Prior Publication Data

US 2019/0147993 A1 May 16, 2019

Related U.S. Application Data

(60) Provisional application No. 62/336,779, filed on May 16, 2016.

(51) Int. Cl.
*G16H 15/00* (2018.01)
*G16H 10/60* (2018.01)
(Continued)

(52) U.S. Cl.
CPC ............ *G16H 15/00* (2018.01); *G06N 20/00* (2019.01); *G16H 10/60* (2018.01); *G16H 50/70* (2018.01)

(58) Field of Classification Search
CPC ........ G16H 15/00; G16H 10/60; G16H 50/70; G06N 20/00
See application file for complete search history.

(56) References Cited

U.S. PATENT DOCUMENTS 7,284,191 B2 * 10/2007 Grefenstette ........... G06F 16/30 715/230
9,842,113 B1 * 12/2017 Sorvillo ................ G06F 16/156
(Continued)

FOREIGN PATENT DOCUMENTS

WO 2007043997 A1 4/2007
WO 2012122122 A1 9/2012
WO 2012123829 A1 9/2012

*Primary Examiner* — Jay M. Patel

(57) ABSTRACT

Instructions (108) cause a processor (104) to: classify a clinical report for a subject under evaluation by one of anatomical organ or disease; identify and retrieve clinical reports for the same subject from the healthcare data source (s); group the retrieved clinical report by one of anatomical organ or disease; select a group of the clinical report, wherein the group includes reports for a same or related one of the anatomical organ or the disease; build a model that predicts semantic relationships between nodes in the reports in the selected group of reports based on one or more of extracted parameters or keywords; compare one of the parameter values or the keywords across the reports using the model; construct a graphical timeline of the reports; highlight differences in the parameter values or the keywords based on a result of the compare; and visually present the graphical timeline with the highlighted differences.

20 Claims, 6 Drawing Sheets

(51) Int. Cl.
*G16H 50/70* (2018.01)
*G06N 20/00* (2019.01)

(56) References Cited

U.S. PATENT DOCUMENTS

2003/0083914 A1* 5/2003 Marvin, III ............ G06Q 40/04 705/37
2006/0024654 A1* 2/2006 Goodkovsky ............ G09B 7/02 434/350
2006/0129538 A1* 6/2006 Baader .................. G06F 16/951
2006/0136270 A1* 6/2006 Morgan ................. G16H 70/00 715/255
2007/0112845 A1* 5/2007 Gilmour ................. G06F 21/31 707/999.102
2008/0177578 A1 7/2008 Zakim
2008/0201280 A1* 8/2008 Martin ................... G16H 30/20 706/45
2008/0275731 A1* 11/2008 Rao ........................ G16H 10/60 705/3
2008/0313000 A1* 12/2008 Degeratu ............... G06Q 10/06 705/319
2009/0132653 A1* 5/2009 Niazi ................... G06Q 10/103 709/204
2009/0307162 A1* 12/2009 Bui ........................ G06N 5/022 706/54
2010/0131293 A1 5/2010 Linthicum et al.
2010/0159438 A1* 6/2010 German ............ G06F 16/24573 434/433
2010/0169983 A1* 7/2010 Horr ....................... G06F 21/84 726/28
2011/0004595 A1 1/2011 Yamagishi et al.
2011/0054946 A1* 3/2011 Coulter .................. G16H 30/20 705/2
2011/0119075 A1* 5/2011 Dhoble .................. G06Q 50/22 705/2
2011/0236870 A1* 9/2011 Chinosornvatana ..... G09B 7/08 434/322
2011/0288877 A1* 11/2011 Ofek ...................... G16H 50/20 707/661
2012/0060216 A1* 3/2012 Chaudhri ............... G16H 70/00 726/21
2012/0191793 A1* 7/2012 Jakobovits ............ G06F 19/321 709/206
2012/0215560 A1* 8/2012 Ofek ...................... G06Q 10/10 705/3
2012/0239671 A1* 9/2012 Chaudhri ............... G16H 50/70 707/756
2012/0303501 A1* 11/2012 Chung ................... G06Q 40/08 705/35
2013/0173306 A1 7/2013 Sasidhar
2013/0290323 A1* 10/2013 Saib ...................... G06F 16/113 707/E17.014
2014/0025732 A1* 1/2014 Lin ....................... H04L 67/306 709/204
2014/0172996 A1* 6/2014 Deeter .................. H04L 51/224 709/206
2014/0350961 A1* 11/2014 Csurka ................... G16H 10/60 705/3
2015/0032464 A1* 1/2015 Vesto ..................... G16H 50/20 705/2
2016/0019299 A1 1/2016 Boloor et al.
2016/0378919 A1* 12/2016 McNutt .................. G16H 40/63 705/3

* cited by examiner

CLINICAL REPORT RETRIEVAL AND/OR COMPARISON

CROSS-REFERENCE TO PRIOR APPLICATIONS

This application is the U.S. National Phase application under 35 U.S.C. § 371 of International Application No. PCT/EP2017/060478, filed on May 3, 2017, which claims the benefit of U.S. Provisional Application No. 62/336,779, filed May 16, 2016. These applications are hereby incorporated by reference herein, for all purposes.

FIELD OF THE INVENTION

The following generally relates to clinical report retrieval and/or comparison.

BACKGROUND OF THE INVENTION

Clinical text reports describe details from clinical processes such as admission, discharge, routine ward rounds, imaging studies, and laboratory reports investigations. These reports contain different types of information on patient scenarios (e.g., diagnoses, treatment plans, prognosis, etc.), including unstructured patient details with valuable contextual insight into the past and current health scenarios, and structured data, which has high fidelity and is typically measured periodically. Structured values (measurements) generally allow clinicians to make prompt assessments of patient states towards appropriate interventions. In addition, such values can be used to determine treatment efficacy and predict the effectiveness of future interventions. Understanding patient scenarios described in clinical reports and interpreting structured data (values) in context of unstructured details within the same reports and other related reports for a specific patient facilitates quality healthcare.

Electronic medical records (EMRs) and patient dashboards notify clinicians when a new report has been created. EMR systems offer functionalities to access clinical reports via queries to large databases. In some systems, the user interface includes hyperlinks (representing database queries) through which clinical reports can be accessed. Clinical reports resulting from such queries are presented as text files or scanned documents to users who subsequently review and interpret the contents. Manually reviewing and interpreting clinical reports is often time consuming and prone to human errors. Furthermore, accessing archived clinical reports in most EMR systems can be very challenging due to technical bottlenecks, and such systems often do not provide functionalities to automatically compare longitudinal reports to extract clinically relevant connections that can inform clinicians on overall patient acuity and support clinical decision making.

SUMMARY OF THE INVENTION

Aspects of the present application address the above-referenced matters and others.

According to one aspect, a system includes a healthcare data source(s) and a computing system with a memory device configured to store instructions, including a clinical report retrieval and/or comparison module. The processor that executes the instructions, which causes the processor to: classify a clinical report for a subject under evaluation by one of anatomical organ or disease; identify and retrieve clinical reports for the same subject from the healthcare data source(s); group the retrieved clinical reports by one of anatomical organ or disease; select a group of the clinical report, wherein the group includes reports for a same or related one of the anatomical organ or the disease; build a model that predicts semantic relationships between the reports in the selected group of reports based on one or more of extracted parameters or keywords; compare one of the parameter values or the keywords across the reports using the model; construct a graphical timeline of the reports; highlight differences in the parameter values or the keywords based on a result of the compare; and visually present the graphical timeline with the highlighted differences.

In another aspect, a method includes classifying, with a processor, a clinical report for a subject under evaluation by one of anatomical organ or disease, identifying and retrieving, with the processor, clinical reports for the same subject from the healthcare data source(s), and grouping, with the processor, the retrieved clinical reports by one of anatomical organ or disease, and selecting, with the processor, a group of the clinical report, wherein the group includes reports for a same or related one of the anatomical organ or the disease. The method further includes building, with the processor, a model that predicts semantic relationships between the reports in the selected group of reports based on one or more of extracted parameters or keywords, comparing, with the processor, one of the parameter values or the keywords across the reports using the model, constructing, with the processor, a graphical timeline of the reports, highlighting, with the processor, differences in the parameter values or the keywords based on a result of the compare, and visually presenting, with the processor, the graphical timeline with the highlighted differences.

In another aspect, a non-transitory computer readable medium is encoded with computer executable instructions, which, when executed by a processor of a computer, cause the computer to: classify a clinical report for a subject under evaluation by one of anatomical organ or disease, identify and retrieve clinical reports for the same subject from the healthcare data source(s), group the retrieved clinical reports by one of anatomical organ or disease, select a group of the clinical report, wherein the group includes reports for a same or related one of the anatomical organ or the disease, build a model that predicts semantic relationships between the reports in the selected group of reports based on one or more of extracted parameters or keywords, compare one of the parameter values or the keywords across the reports using the model, construct a graphical timeline of the reports, highlight differences in the parameter values or the keywords based on a result of the compare, and visually present the graphical timeline with the highlighted differences.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
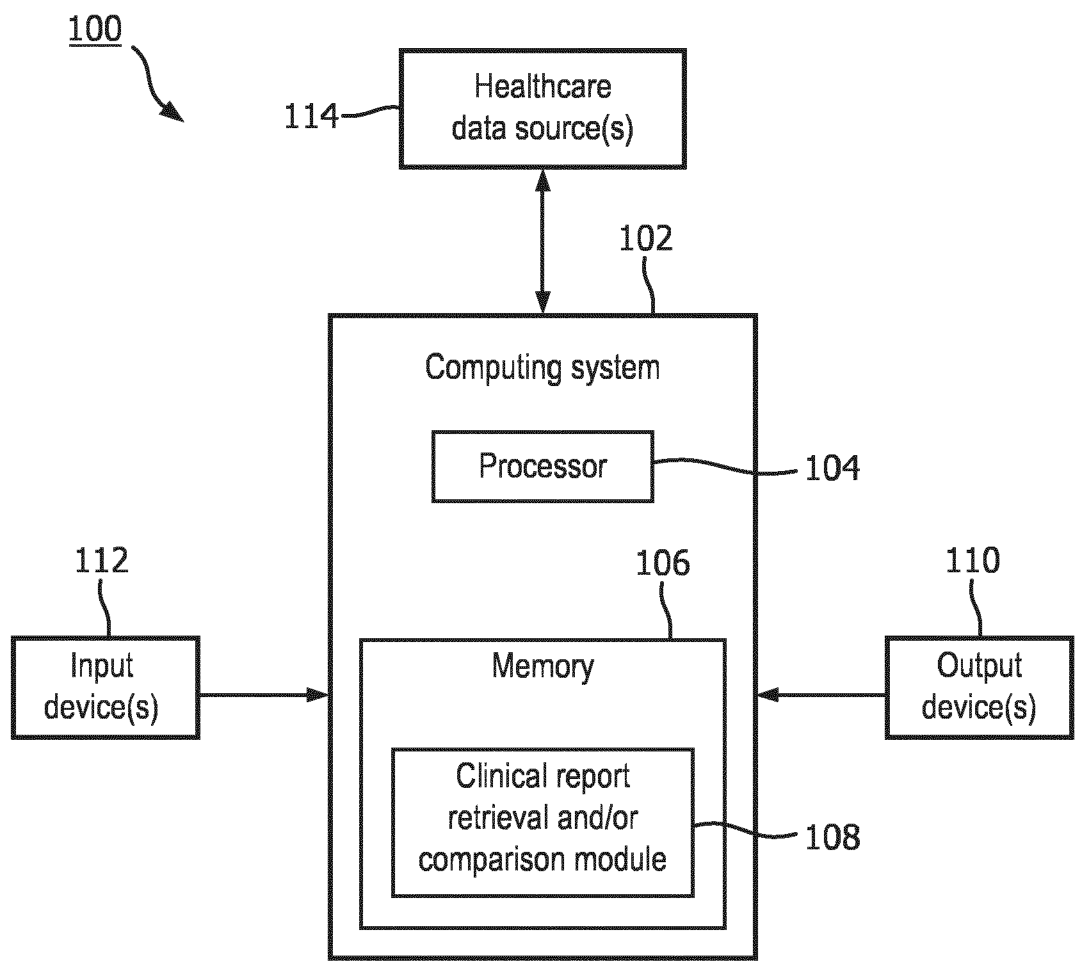
FIG. 1 schematically illustrates an example computing system with a clinical report retrieval and/or comparison module.

FIG. 1 illustrates an example system 100. The system 100 includes a computing system 102 with at least one processor 104 (e.g., a microprocessor, a central processing unit, etc.) that executes at least one computer readable instruction stored in a computer readable storage medium ("memory") 106, which excludes transitory medium and includes physical memory and/or other non-transitory medium. The instruction, in this example, includes a clinical report retrieval and/or comparison module 108 with corresponding computer executable instructions. The computing system 102 also includes output device(s) 110, such as a display monitor, portable memory, a network interface, etc., and an input device(s) 112 such as a mouse, keyboard, a network interface, etc. One or more healthcare data sources 114 stores data such as electronically formatted clinical reports.

In one non-limiting example, the instructions of the clinical report retrieval and/or comparison module 108, when executed by the at least one processor 104, cause the at least one processor 104 to retrieve relevant longitudinal reports from the one or more healthcare data sources 114 and/or compare certain patient details in these reports to generate clinically relevant semantic information networks. Comparing a current report with an older report of the same type (e.g. current and past EKG reports) is useful in understanding how the patient condition has changed over time. In addition, the current report can be compared to other related reports such as comparing the current EKG report to a previous echocardiogram (echo) report. Such comparisons can assist clinicians in constructing a model of patient scenarios towards better understanding of causal relationships, patient acuity, potential treatment options, intervention effectiveness, and prognosis.

Figure 2:
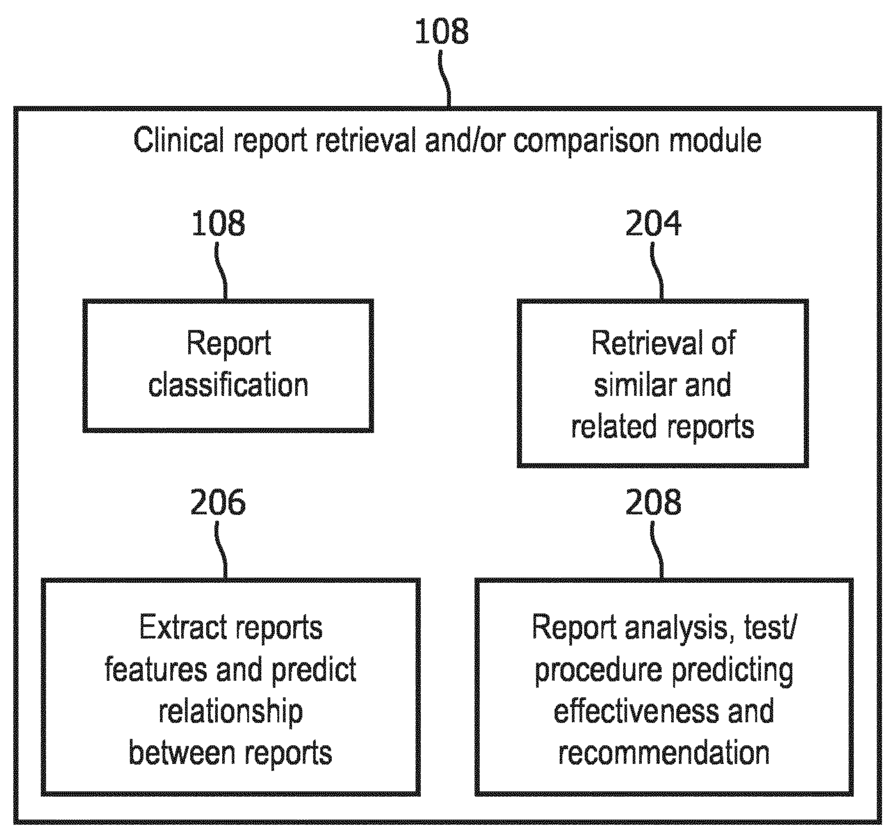
FIG. 2 schematically illustrates an example of the clinical report retrieval and/or comparison module.

An example of the clinical report retrieval and/or comparison module 108 is shown in FIG. 2 and includes a report classification (or first) sub-module 202, a retrieval of similar and related reports (or second) sub-module 204, an extract reports features and predict relationship between reports (or third) sub-module 206, and a report analysis, test/procedure predicting effectiveness and recommendation (or fourth) sub-module 208. The first sub-module 202 classifies a new report based on report type and/or the body system it relates to (e.g. an echo report relates to the cardiovascular system). The second sub-module 204 finds related reports for the selected patient from the healthcare data source(s) 114. The third sub-module 206 extracts quantitative (structured) information along with contextual (unstructured) details from the retrieved reports and identifies the semantic relationships across the reports. The fourth sub-module 208 presents the extracted the clinically relevant semantic information and relationships between reports to the user. In one instance, results are visualized and/or used to predict test effectiveness and/or recommend next steps.

A challenge in finding related reports is that different types of reports (labs, imaging studies, procedure notes etc.) might relate to the same issue, and these relationships are not explicit. Relative to retrieving previous reports of the same type for the same patient, retrieving different but related reports (e.g. a lab report and an imaging report to assess renal function) requires an understanding of the issue as well as analyses of the report contents. Hence, to solve this problem the clinical report retrieval and/or comparison module employs an algorithm that can learn the relationships between reports and use that information to predict the relatedness of reports. Machine learning techniques (e.g. Bayesian networks, random forest, support vector machines, etc.) can be used to build models which can learn relationships across various reports. The model would be trained on clinical concepts in the reports and standard clinical ontologies (e.g. the Systematized Nomenclature of Medicine—Clinical Terms, or SNOMED CT) as input features and output the predicted relationship across reports.

A challenge in comparing across various reports is understanding the content of the reports and putting them in a temporal context. Since these reports are typically semi-quantitative, a step in processing the content of the reports is to identify and extract these structured data along with the unstructured (descriptive) information of the patient scenario. Similar structured data types extracted from different reports can be compared to generate trend reports. To compare different data types describing a particular patient scenario, the semantic relationships identified in the reports would be used to generate a contextual interpretation of the clinical picture presented by the patient's condition towards better informed clinical decision-making. A technical challenge which can be mitigated by the clinical report retrieval and/or comparison module includes identification of semantic relationships across reports and automatically categorizing/ranking such relationships based on clinical importance.

Figure 3:
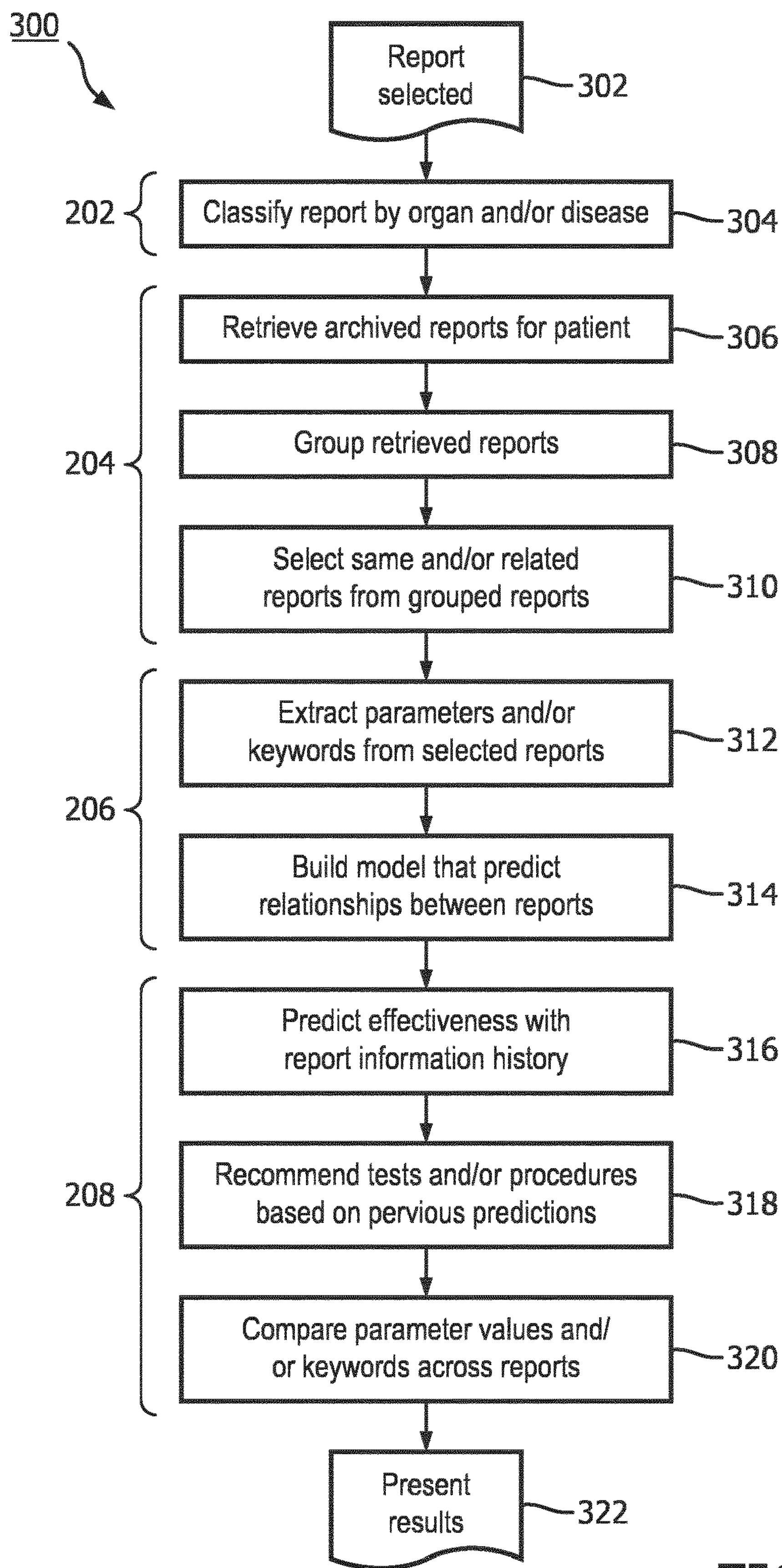
FIG. 3 illustrates an example flow chart for clinical report retrieval and/or comparison.

FIG. 3 schematically illustrates a flow chart 300 for clinical report retrieval and/or comparison. The first and last acts 302 and 322 are performed via a front end user interface, and the acts 304-320 there between are performed via a backend machine learning, which learns from previous reports with known relationships clinically relevant semantic information.

At 302, a user selects a clinical report of interest for a patient. The clinical report is in electronic format and stored in computer memory such as the memory 106, a healthcare data source 114, and/or other memory. The clinical report can be selected using the computing system 102 via a mouse pointer from a list of available reports presented to the user on a display monitor of the output device(s) 110, by typing via a keyboard of the computing system 102 a file name at a command prompt, and/or other known technique. The clinical report may be a most recent or other report for the patient.

At 304, the computing system 102 classifies the selected report. This can be done by using a report type information (e.g., SNOMED CT) code for the report type and final diagnosis and/or information from a report header and/or metadata, which has information on the report source, type and/or other details. The classification categorizes the report based on body system and/or as related to a particular disease. Other classifications are contemplated herein.

At 304 is performed by the report classification (or first) sub-module 202 of the clinical report retrieval and/or comparison module 108.

At 306, the computing system 102 retrieves related archived reports for the patient from the healthcare data source(s) 114. For example, in one non-limiting instance, the computing system 102 accesses a health care data source of the healthcare data source(s) 114 such as a report database of a hospital and retrieves all reports for the selected patient using a unique medical record number (MRN) and/or other identifier unique to the patient.

At 308, the computing system 102 groups each retrieved archived report. For example, in one non-limiting instance, the retrieved archived reports are classified using the approach described in act 304 and/or other approach into either body system-based groups or disease-based groups. Other groupings are also contemplated herein.

At 310, same type and/or related reports from the grouped reports are selected. To select a same type of report, the computing system 102 uses report type information (e.g. SNOMED CT codes) to find an exact match. Related reports are broadly defined as previous reports belonging to a same body system and/or referring to a same disease. To select a related report, the computing system 102 matches the body system and/or disease type information to the relevant information from the selected report.

Acts 306, 308 and 310 are performed by the retrieval of similar and related reports (or second) sub-module 204 of the clinical report retrieval and/or comparison module 108.

At 312, the computing system 102 extracts parameters and/or keywords from the selected retrieved reports. In one instance, this includes extracting quantitative information (e.g., measurements, lab values, etc.) in these reports as well as context of such values with respect to the patient scenario. A natural language processing (NLP) pipeline can be used to extract key structured and unstructured information.

Figure 4:
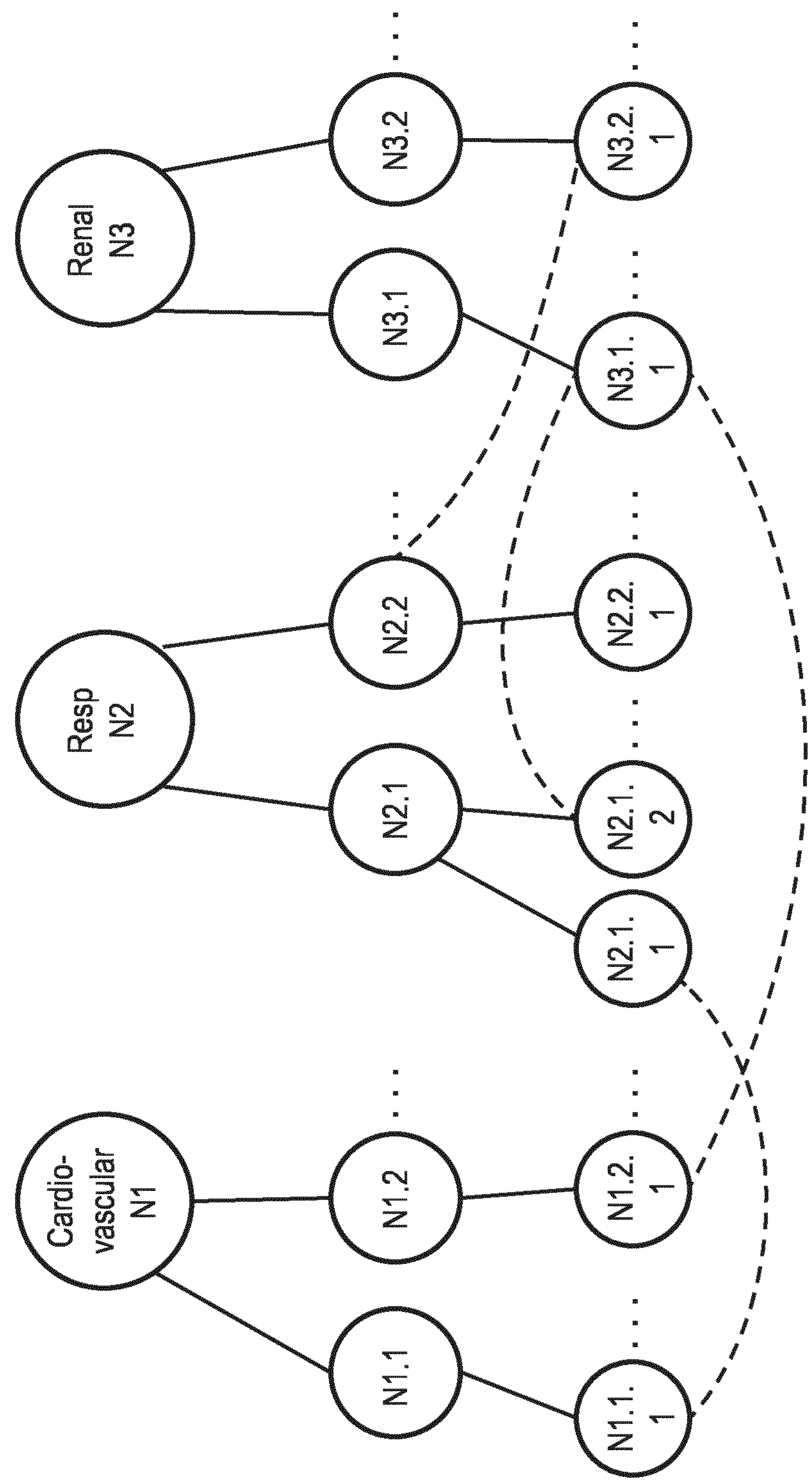
FIG. 4 schematically illustrates an example supervised approach to building a semantic relationship network.
Figure 5:
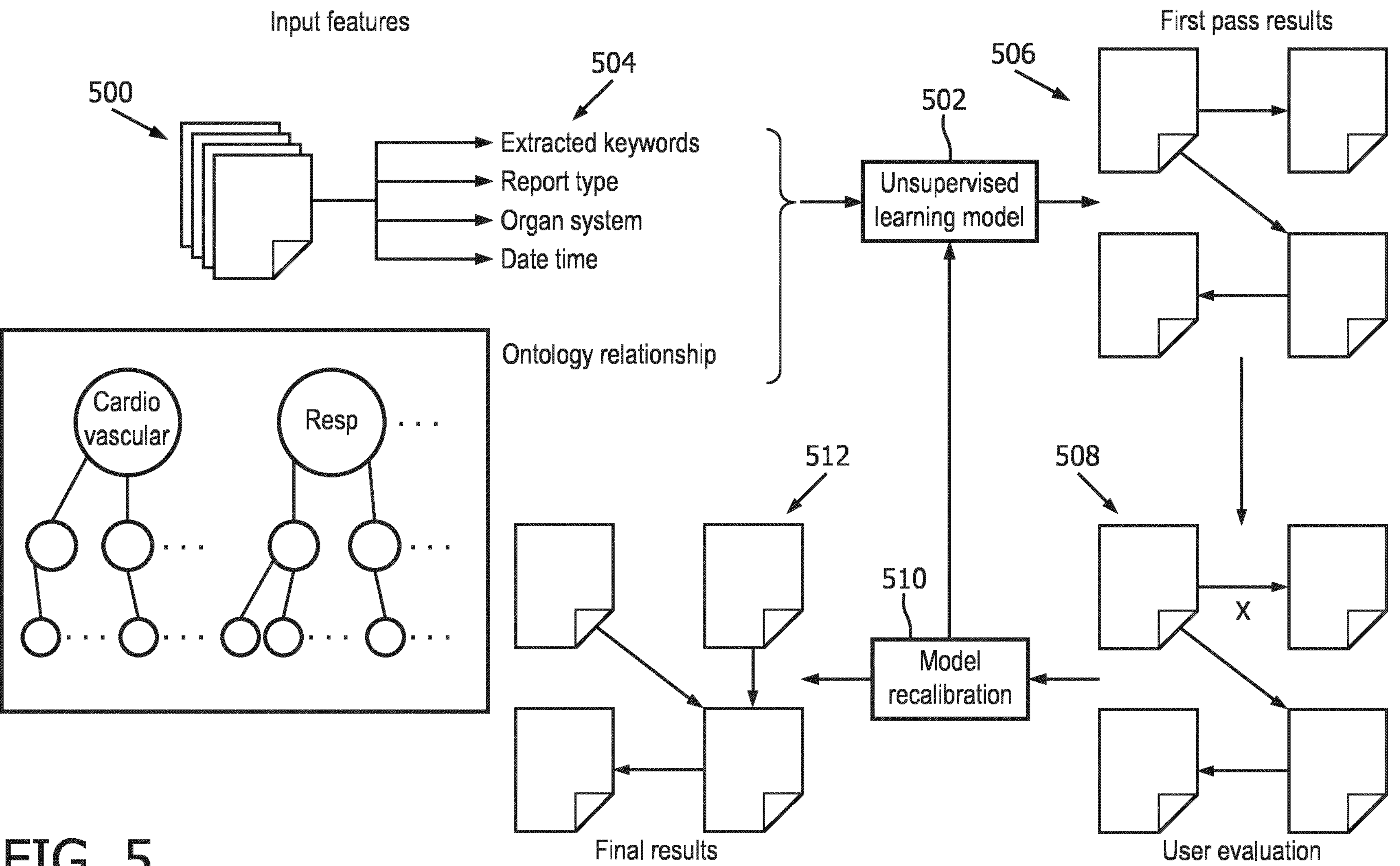
FIG. 5 schematically illustrates an example semi-supervised approach to building a semantic relationship network.

At 314, the computing system 102 determines a semantic relationship network, which will connect the various reports selected. FIGS. 4 and 5 illustrated two non-limiting approaches to building a semantic relationship network. Other approaches are also contemplated herein.

FIG. 4 schematically illustrates an approach based on supervised machine learning that trains on corpora of annotated reports indicated semantic concept relationships. To build this using a machine learning model for generating the semantic relationship network using supervised learning, a network of anatomical and physiological concepts in clinical reports are manually generated by domain experts. From an existing parent-child relationship in the standard clinical ontologies (e.g. SNOMED CT tree), clinical domain experts would manually develop a network by linking related child nodes from various parent nodes to create new edges in a semantic graph.

In FIG. 4, N1 represents the cardiovascular system, N2 represents the respiratory system, N3 represents the renal system, . . . . The nodes directly under the organ systems N1, N2, N3, . . . are respectfully numbered N1.1, N1.2 . . . , N2.1, N2.2 . . . , N3.1, N3.2 . . . . The nodes directly under the N1.1, N1.2 . . . , N2.1, N2.2 . . . , N3.1, N3.2 . . . are respectfully numbered N1.1.1, . . . , N1.2.1, . . . , N2.1.1, . . . , N2.2.1, . . . , N3.1.1, . . . , N3.2.1 . . . and indicate a hierarchical relationship. The ontology is shown in FIG. 4 as a tree structure in solid lines. The dashed lines represent the manually linked nodes.

The anatomical and physiological concept networks can then be used to identify the relationship between reports. Keywords and clinical concepts extracted from the reports by the NLP pipeline would be connected based on the concept networks. The relationship identified by the concept networks would be used to semantically link the reports and contextualize the contents for better understanding of the patient's overall clinical picture.

FIG. 5 schematically illustrates another approach which is based on semi-supervised learning. In this approach, the computing system 102 initially learns the semantic relationships across clinical reports 500 in an unsupervised manner 502. The input 504 features to the computing system 102 are the NLP extracted structured and unstructured information. In addition, features obtained from the report header such as body/organ system information, specific anatomical or physiological details, the type of report (e.g. type of imaging study or lab report or procedure report) and/or a date of a report are included. Another feature would be the relationship between the different anatomical or physiological ontologies.

All this information will be used as features to build a concept relationship model across reports. An example, first pass 506 uses arrows to show relationships between reports. The results of this initial unsupervised learning would be presented to the clinical domain experts via a display monitor output device 110, as shown at 508, and the expert will evaluate the accuracy of the semantic relationships. In the illustrated example, the user removes a relationship, which is shown through an "X" under the arrow between the top two reports. Based on the experts' evaluation, the computing system 102 will adjust via a model recalibration 510 the network parameters to develop a more accurate network 512 of concepts and reports. This model can now be used to identify new semantic relationships across other groups of reports.

The computing system 102 will learn over time with more data and further refine the concept network, e.g., via a feedback 514. Moreover, based on the knowledge corpus of the computing system 102, computing system 102 can generate new hypothesis regarding previously unknown concept relationships. Based on the extracted concepts and learnt semantic relationships, a distance score will be calculated to measure the relatedness of the retrieved reports to the initially selected report. The reports would then be ranked and filtered based on how far they are from the initial report.

For example, in one instance the content (keywords) of the user-selected report is compared to a set of keywords in all candidate related reports, and a mean distance score is computed based on how semantically similar the set of keywords for each candidate report is to the content of the original report. The lower the mean distance score, the more the likelihood of a candidate report being similar to the original report. The mean distance score is then used to rank all related reports. Additionally, any report with a distance score above a value of an empirical distance score threshold is considered remotely related to the original report and vice versa.

Returning to FIG. 3, acts 312 and 314 are performed by the extract reports features and predict relationship between reports (or third) sub-module 206 of the clinical report retrieval and/or comparison module 108.

At 316, an effectiveness is predicted with report information history. For example, in one non-limiting instance for each report on a test/imaging study/procedure etc. computing system 102 finds the effectiveness of that test/imaging study/procedure from previously published studies from an external publications database. The computing system 102 would then display the sensitivity and specificity values for that particular test in detecting the condition of interest. This would help the physician make informed decisions on appropriate investigative procedures for specific clinical scenarios. Optionally, the cache of report relationships can be used to provide information on procedure effectiveness based on published literature.

At 318, tests and/or procedures are recommended based on previous predictions. For example, in one non-limiting instance the computing system 102 recommends a most optimal next steps for a given patient scenario. The computing system 102 would cache the semantic relationship between reports from different searches towards building a corpus of connected reports. When the user wants recommendations on the next step, the system can show a list of most relevant tests/procedures based on these cached networks of semantic information. Optionally, the cache of report relationships can be used to recommend most effective investigative procedure for the patient given previous reports and published literature.

At 320, the parameter values and/or keywords are compared across reports in a timeline identifying any changes. For example, in one non-limiting instance the identified semantic relationships (from the previous component) and the report timestamps are used to order the reports in a meaningful temporal manner. Certain concepts and their semantic relationships would be used to generate a brief summary of the patient scenario. This summary would be presented to the user along with the group of related reports with the relevant sections highlighted.

Figure 6:
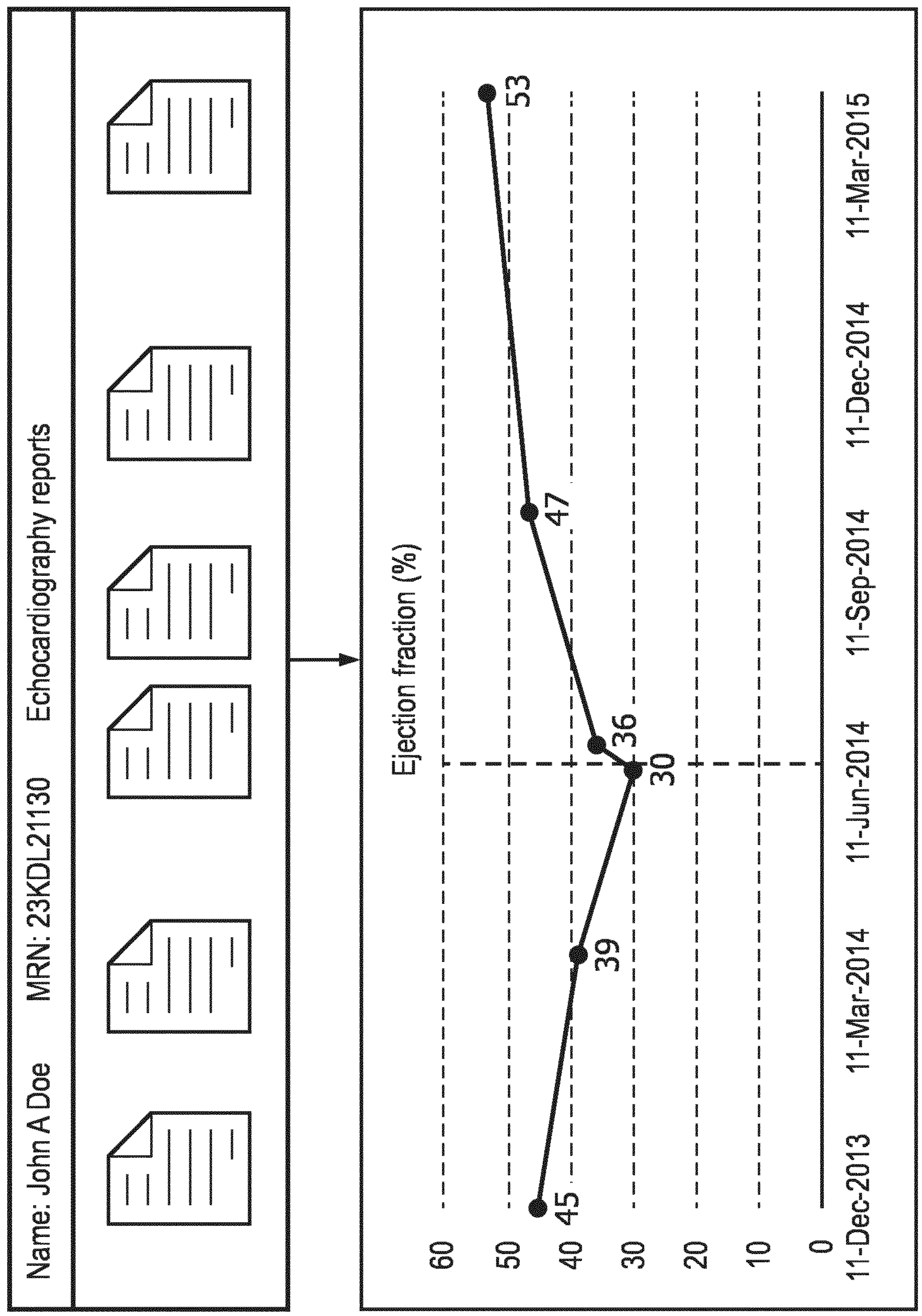
FIG. 6 shows an example in which parameter values are shown in a timeline.

For reports of the same type, parameter values can be shown in a timeline and/or a trend graph. FIG. 6 shows an example in which parameter values are shown in a timeline. For this example, ejection fraction information is extracted from multiple echo reports of the patient and graphed over time. The shaded portion of the graph indicates reduced ejection fraction. The dashed line in the graph indicates intervention to improve ejection fraction.

Acts 316, 318 and 320 are performed by the report analysis, test/procedure predicting effectiveness and recommendation (or fourth) sub-module 208 of the clinical report retrieval and/or comparison module 108.

At 322, the results are visually presented via a display monitor of the output device(s) 110. The displayed data presents a comparison across reports and highlights certain findings related to the comparison.

The following provides a non-limiting example use case. The example use case is for evaluating the effectiveness of treatment for a pancreatic tumor. An abdominal x-ray of a patient with prolonged constipation showed multiple 'air-fluid levels'. Further investigation via an abdominal CT scan revealed a pancreatic mass obstructing the second part of the duodenum. A Whipple procedure (pancreatoduodenectomy) was performed to remove the tumor. Postoperative abdominal X-ray revealed no air fluid levels. Subsequent abdominal CT also showed no sign of the mass.

When a clinician accessed the postoperative abdominal CT report via the computing system 102 to review the patient history related to this report, the computing system 102 retrieved the above mentioned X-ray and CT reports along with the procedure notes. The computing system 102 arranged the reports in a timeline and extracted the relevant concepts. The parameters in the two X-ray reports and two CT reports were compared. The changes in certain findings in these reports were highlighted. In addition, quantitative data with multiple values were graphed.

The method herein may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium.

The approach described herein can improve computing system performance. For example, the computing system 102 can store the retrieved reports and/or semantic relationship in cache memory. Subsequently, if the same report is selected again, e.g., by a different clinician, etc., the computing system 102 can automatically retrieve the related reported and/or the semantic relationship stored in the cache memory, which can be part of the memory 106 and/or memory. This reduces the processing cycles required to retrieve these reports and/or determine the semantic relationship relative to having to identify and retrieve these reports and again determine the semantic relationship. In other words, it can reduce the number of processing cycles required to construct a meaningful output.

A result of the approach described herein can also drive another device. For example, the computing system 102 can transmit a signal indicative of the semantic relationship to another device, which causes the other device to retrieve and return and/or display a suitable clinical protocol stored in a protocol database. This clinical protocol may be different to the current clinical protocol being followed. Without this transmission controlling the other device, the original protocol would still be followed. In one instance, the other protocol includes an act performed by a machine, the transmission causes the device performing that act to perform the act. For example, the transmission may cause a device in a laboratory to perform another test on a sample being processed.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A system, comprising:

a healthcare data source; and a computing system, comprising:

a memory device configured to store instructions a processor that executes the instructions, which cause the processor to:

classify a clinical report, for a subject under evaluation, by one of an anatomical organ or disease;

identify and retrieve clinical reports for the same subject from the healthcare data source;

group the retrieved clinical reports by one of anatomical organ or disease;

select a group of the clinical reports, wherein the group includes reports for a same or related one of the anatomical organ or the disease;

build a model that predicts semantic relationships between nodes in the reports in the group of clinical reports based on one or more of extracted parameters or keywords;

compare one of the one or more extracted parameters or the keywords across the reports using the model;

construct a graphical timeline of the reports; highlight difference in values of the one or more extracted parameters or the keywords based on a result of the compare;

identify one or more tests that can be applied to the subject based on the one or more of the extracted parameters or the keywords;

determine a sensitivity value and a specificity value of the at least one of the one or more identified tests;

visually present the comparison of the one or more extracted parameters or keywords and the highlighted differences related to the comparison in the graphical timeline; and visually present the sensitivity value and the specificity value.

2. The system of claim 1, wherein instructions further cause the processor to use a supervised machine learning approach or a semi-supervised learning approach to build the model.

3. The system of claim 2, wherein: the supervised machine learning approach is trained with a corpora of annotated reports with known semantic relationships; and the instructions further cause the processor to link a network of anatomical and physiological concepts across the clinical report based on the known semantic relationships.

4. The system of claim 3, wherein the instructions further cause the processor to predict semantic relationships between the reports using the link between the network of anatomical and physiological concepts and the clinical report.

5. The system of claim 2, wherein the instructions further cause the processor to build the model based on one or more of extracted structured and unstructured information from one or more of body/organ system information obtained from a report header, specific anatomical or physiological details, a type of report, or a relationship between different anatomical or physiological ontologies.

6. The system of claim 5, wherein the instructions further cause the processor to visually present the model; receive feedback about a correctness of the semantic relationships; and update the model based on the feedback, and constructs a final model based on the model.

7. The system of claim 5, wherein the instructions further cause the processor to build the model based on previously received feedback.

8. The system of claim 1, wherein the instructions further cause the processor to predict an effectiveness of the model based on report information history from previously published studies from an external publications database.

9. The system of claim 1, wherein the instructions further cause the processor to recommend at least one of a test or a procedure based on previous predictions through a list of most relevant tests or procedures based on the semantic relationships.

10. The system of claim 1, wherein the instructions further cause the processor to: transmit a signal indicative of the graphical timeline with the differences to a device, which causes the device to retrieve and return or present a suitable clinical protocol for the subject; or perform a processing act on a sample for the subject.

11. The system of claim 1, wherein the semantical relationships are stored in a memory and the processor is adapted to use the semantic relationships instead of building another model in response to a different evaluation for the same subject by a different entity.

12. A method, comprising:

classifying, with a processor, a clinical report for a subject under evaluation by one of anatomical organ or disease;

identifying and retrieving, with the processor, clinical reports for the same subject from one or more healthcare data sources;

grouping, with the processor, the clinical reports by one of an anatomical organ or disease;

selecting, with the processor, a group of the clinical reports, wherein the group includes reports for a same or related one of the anatomical organ or the disease;

building, with the processor, a model that predicts semantic relationships between nodes of ontology branches in the reports in the group of clinical reports based on one or more of extracted parameters or keywords;

comparing, with the processor, values from one or more of the extracted parameters or the keywords across the reports using the model;

constructing, with the processor, a graphical timeline of the reports;

highlighting, with the processor, differences in the values from the one or more of the extracted parameters or the keywords based on a result of the compare;

identifying, with the processor, one or more tests that can be applied to the subject based on the one or more of the extracted parameters or the keywords;

determining a sensitivity value and a specificity value of the at least one of the one or more identified tests;

visually presenting, with the processor, the comparison of the one or more extracted parameters or keywords and the highlighted differences related to the comparison in the graphical timeline; and visually presenting, with the processor, the sensitivity value and the specificity value.

13. The method of claim 12, wherein building the model includes predicting the semantic relationships between known links between a network of anatomical and physiological concepts and the clinical report; and wherein the method further comprises: creating the links through supervised machine learning with a corpora of annotated reports with known semantic relationships.

14. The method of claim 12, further comprising:

building an initial model based on one or more of extracted structured and unstructured information;

visually presenting the initial model;

receiving feedback about the semantic relationships in the initial model; and changing the semantic relationships in the initial model based on the feedback, which builds the model.

15. A tangible, non-transitory computer readable medium encoded with computer executable instructions, which, when executed by a processor of a computer, cause the computer to:

classify a clinical report for a subject under evaluation by one of anatomical organ or disease;

identify and retrieve clinical reports for the same subject from a healthcare data source;

group the retrieved clinical reports by one of an anatomical organ or disease;

select a group of the clinical reports, wherein the group includes reports for a same or related one of the anatomical organ or the disease;

build a model that predicts semantic relationships between the reports in the group of reports based on one or more of extracted parameters or keywords;

compare values of the one or more extracted parameters or the keywords across the reports using the model;

construct a graphical timeline of the reports;

highlight differences in the values of the one or more extracted parameters or the keywords based on a result of the compare;

identify one or more tests that can be applied to the subject based on the one or more of the extracted parameters or the keywords;

determine a sensitivity value and a specificity value of the at least one of the one or more identified tests;

visually present the comparison of the one or more extracted parameters or keywords and the highlighted differences related to the comparison in the graphical timeline; and visually present the sensitivity value and the specificity value.

16. The tangible, non-transitory computer readable medium of claim 15, wherein the instructions further cause the processor to use a supervised machine learning approach or a semi-supervised learning approach to build the model.

17. The tangible, non-transitory computer readable medium of claim 16, wherein the supervised machine learning approach is trained with a corpora of annotated reports with known semantic relationships; and the instructions further cause the processor to link a network of anatomical and physiological concepts across the clinical report based on the known semantic relationships.

18. The tangible, non-transitory computer readable medium of claim 17, wherein the instructions further cause the processor to predict semantic relationships between the clinical report using the link between the network of anatomical and physiological concepts and the clinical reports.

19. The tangible, non-transitory computer readable medium of claim 16, wherein the instructions further cause the processor to build the model based on one or more of extracted structured and unstructured information from one or more of body/organ system information obtained from a report header, specific anatomical or physiological details, a type of report, or a relationship between different anatomical or physiological ontologies.

20. The tangible, non-transitory computer readable medium of claim 19, wherein the instructions further cause the processor to visually present the model; receive feedback about a correctness of the semantic relationships; and update the model based on the feedback, and constructs a final model based on the model.

* * * * *